United States Patent [19]

Alexander et al.

[11] E Patent Number: Re. 32,338

[45] Reissued Date of Patent: Jan. 27, 1987

[54] GRIPPER MEMBER FOR RETENTION OF A PLASTIC TUBE

[75] Inventors: John B. Alexander, Evanston; Michael T. Dennehey, Arlington Heights; Richard J. Greff, Ingleside; John M. Munsch, Libertyville, all of Ill.

[73] Assignee: Baxter Travenol Laboratories, Inc., Deerfield, Ill.

[21] Appl. No.: 410,749

[22] Filed: Aug. 23, 1982

Related U.S. Patent Documents

Reissue of:

[64] Patent No.: 4,227,730
Issued: Oct. 14, 1980
Appl. No.: 43,061
Filed: May 29, 1979

[51] Int. Cl.[4] ..... C25B 7/02

[52] U.S. Cl. ..... 294/16; 128/346

[58] Field of Search ..... 294/16, 27, 28, 31, 294/104, 103; 81/3.44, 3.41, 3.42; 128/346, 321, 322; 257/9, 10

[56] References Cited

U.S. PATENT DOCUMENTS

| | | | |
|---|---|---|---|
| 1,413,690 | 4/1922 | Slocum | 24/232 R |
| 2,468,823 | 5/1949 | Housepian | 128/346 |
| 3,461,876 | 8/1969 | Miller . | |
| 3,706,312 | 12/1972 | Melges | 128/346 |
| 3,862,776 | 1/1975 | Sims et al. | 294/16 |
| 3,942,228 | 3/1976 | Buckman et al. . | |
| 4,170,995 | 10/1979 | Levine et al. . | |
| 4,193,174 | 3/1980 | Stephens | 128/346 |

*Primary Examiner*—James B. Marbert
*Attorney, Agent, or Firm*—Paul C. Flattery; Garrettson Ellis; Daniel D. Ryan

[57] ABSTRACT

A gripper member comprises an openable and closable pair of handles interconnected by a hinge member. Each handle defines, adjacent its hinge member, an arcuate recess positioned to face the corresponding recess of the other handle and defining gripping projections therein. A wall member is positioned longitudinally on each handle to cross each arcuate recess, both wall members being positioned at the same side of their respective recesses. Accordingly, a plastic tube may be surrounded and gripped in the arcuate recesses of the handles for rotational retention thereof as a connector member is inserted into or withdrawn from the tube. At the same time, the wall members pinch the tube into closed, sealed relation with the handles in closed position.

17 Claims, 4 Drawing Figures

FIG. 1
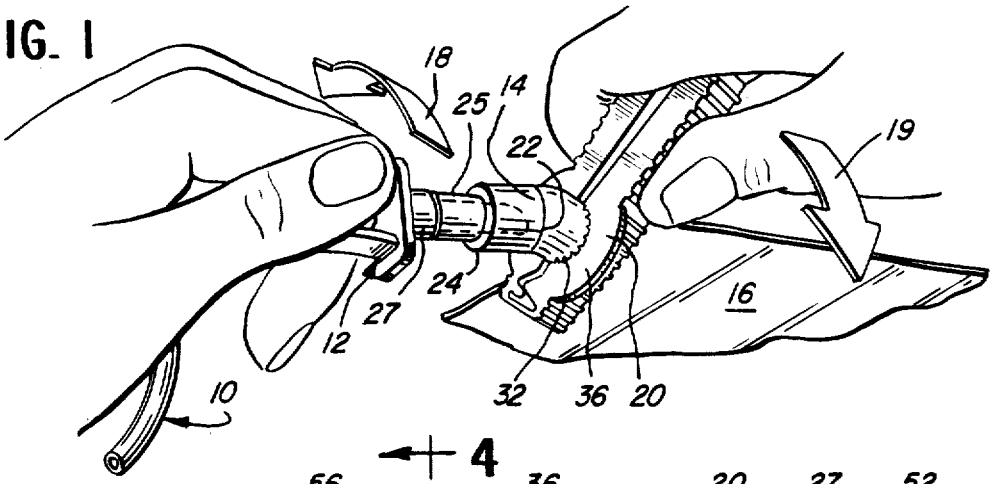
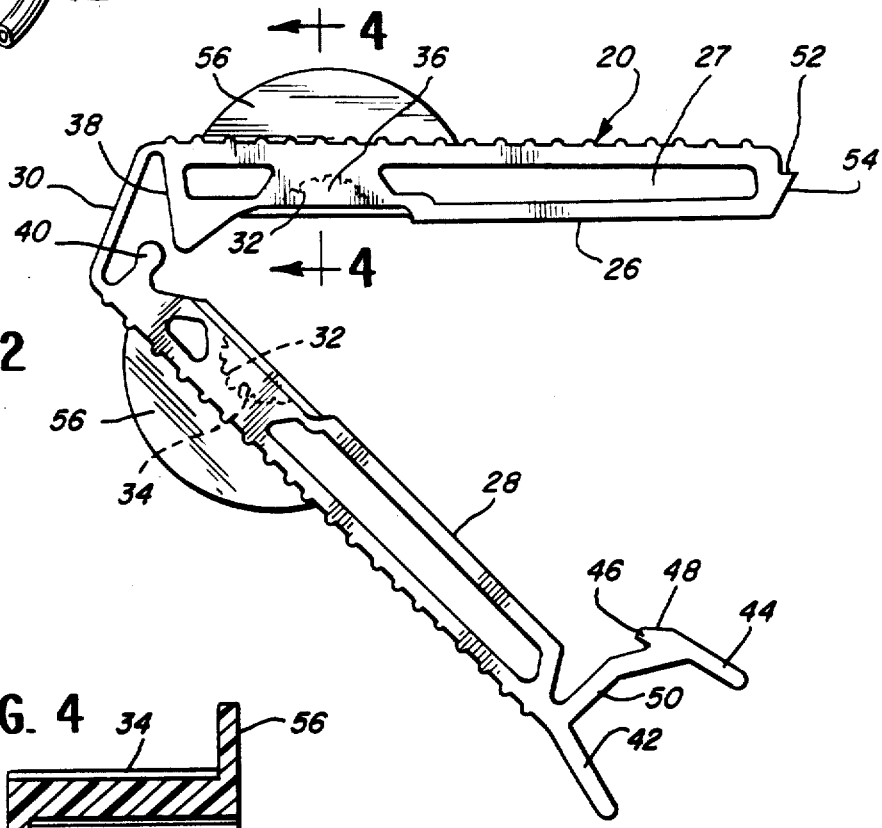
FIG. 2
FIG. 4
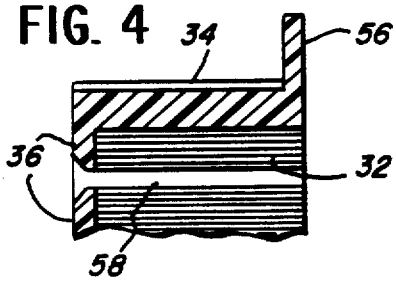
FIG. 3
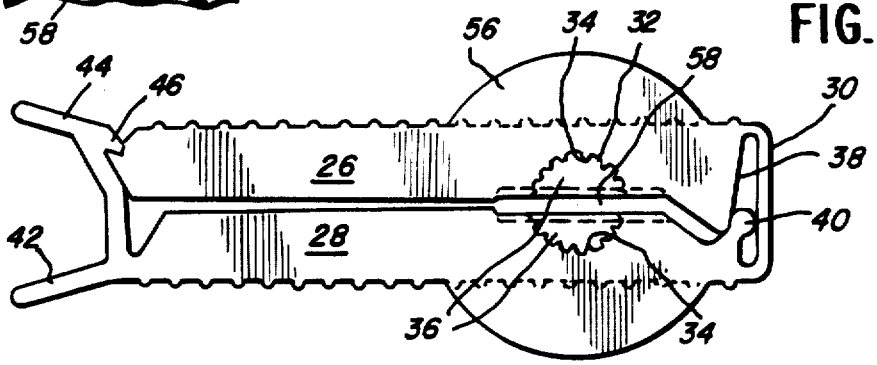

GRIPPER MEMBER FOR RETENTION OF A PLASTIC TUBE

Matter enclosed in heavy brackets [ ] appears in the original patent but forms no part of this reissue specification; matter printed in italics indicates the additions made by reissue.

BACKGROUND OF THE INVENTION

The technique of peritoneal dialysis has been one technique in which the kidney function of a uremic patient is replaced by dialyzing the peritoneum by inserting peritoneal dialysis solution into the peritoneum of the patient, allowing solute exchange from the blood to the peritoneal dialysis solution through the peritoneum, and then removing the peritoneal dialysis solution.

In a recent development, the technique of continuous ambulatory peritoneal dialysis permits the patient to have a surgically implanted catheter which may be connected intermittently to a peritoneal dialysis transfer set. The transfer set, in turn, connects to a bag of peritoneal dialysis solution, which is emptied through the transfer set into the peritoneal cavity. The patient then is ambulatory, without disconnecting the bag or the transfer set, until the dialysis exchange procedure has taken place, after which the peritoneal dialysis solution is allowed to flow back into the bag, which may then be disconnected from the transfer set.

A description of the continuous ambulator peritoneal dialysis technique may be found in Popovich U.S. application Ser. No. 773,912, filed Mar. 3, 1977 and entitled: "METHOD AND APPARATUS FOR CONTINUOUS AMBULATORY PERITONEAL DIALYSIS", and Dennehey, et al. U.S. application Ser. No. 005,748, filed Jan. 23, 1979, and entitled "SOLUTION CONTAINER FOR CONTINUOUS AMBULATORY PERITONEAL DIALYSIS".

As part of some peritoneal dialysis techniques, it is desirable to make a sterile connection between the solution container, and the transfer set, and then later to break the same connection in an aseptic manner after the container has been refilled with spent peritoneal dialysis solution, for reconnection to another container.

While connections between sets and bags or other containers are routinely made, it turns out that a good, sterile, connection seal between the port tubing of a bag and a spike of a set in a flexible port tubing of a container is very difficult to disconnect. The flexible port tubing is usually not very easily gripped with the fingers, and it turns out to be difficult to get a good grip on it, so that the spike can be twisted out in an aseptic mamner. When a nurse or a technician is using extreme effort to break the connection between the spike of the transfer set and the tubing of a filled bag, it is possible for the fingers to touch the connection in a contaminating way. Also it is possible for the bag of spent solution to spill in the effort of disconnection.

In accordance with this invention, a gripper member is provided for gripping plastic tubing and the like to provide rotational retention to the plastic tubing, plus mechanical advantage so that the effort involved in the rotational retention is easier. It then becomes a much easier matter to simply twist and remove the spike out of the tube while, at the same time, the gripper member holds the tubing of the solution container closed so that solution does not spill.

DESCRIPTION OF THE INVENTION

In accordance with this invention, a gripper member, which may be made of one single integral plastic piece, comprises an openable and closable pair of handles interconnected by a hinge member. Each handle defines, adjacent said hinge member, an arcuate and preferably essentially semi-circular recess positioned to face the corresponding recess of the other handle. Each recess defines gripping projections therein to receive and hold tubing or the like which is placed in the recess.

A wall member is positioned longitudinally on each recess, across each arcuate recess and positioned at the same side thereof. As the result of this, a plastic tube may be surrounded and gripped in the arcuate recesses of the handles for rotational retention thereof, as a connector member is inserted into or withdrawn from the tube. At the same time, the wall members pinch the tube into closed, sealed relation when the tube occupies the recesses with the handles in closed position.

Preferably, one handle of the gripper member defines a rigid, sliding surface adjacent to and facing the hinge member. The other handle defines a rigid projection adapted to abut and slide on the surface as the handles are closed. The effect of this is to stabilize the handles against relative lateral motion, since the width of both the rigid sliding surface and the rigid projection is substantial, and preferably essentially the width of the handles, to suppress rocking or relative sideways motion of the handles as they are closed together. This relative sideways motion could be expected to take place if only the hinge member were present, since the hinge member is generally too flexible to effectively suppress sideways motion of the handles.

It is also preferred for one handle of the gripper member to carry, at its end opposed to the hinge member, and integral pair of pinch arms, and a hook member carried on one of the arms. The other hinge carries at its end opposed to the hinge member a detent member. The hook member is adapted to engage the detent member by a snap-in action, to hold the handles in closed position.

The pinch arms are then adapted to disengage the detent and hook members by manual pinching, to permit opening of the handles.

It is further preferred for each handle of the gripper member to carry a flange positioned longitudinally at one end and one side of the handle, and adjacent the arcuate recesses, to prevent touch contamination of the plastic tube by the fingers while it occupies the recesses.

The gripper member of this invention may be effectively used to hold the flexible tubing port of a solution bag, while a spike of a set or the like is being inserted or removed from the tubing to promote the aseptic and easy disconnection or connection of the components without spilling of the contents of the bag.

In the drawings, FIG. 1 is a fragmentary, perspective view showing a solution bag being gripped by the gripper member of this invention, to facilitate the disconnection of the flexible, tubular port of the bag with a spike of a set, for example, a set in a peritoneal dialysis procedure.

FIG. 2 is a plan view of the gripper member of this invention in open condition.

FIG. 3 is a plan view of the gripper member of FIG. 2 in closed position, taken from the other side.

FIG. 4 is a sectional view taken along lines 4—4 of FIG. 2, but also showing a sectional part of the other handle in closed position.

Referring to the drawings, a fragmentary portion of a solution set 10, defining a conventional penetrating spike 12, is shown in the processs of being disengaged from a flexible, tubular port 14 of a solution bag 16 which has, for example, been utilized in a continuous ambulatory peritoneal dialysis procedure, and is now full of spent dialysis solution.

For such disengagement between spike 12 and port 14, the user endeavors to rotate the spike, for example in a counterclockwise manner as shown by arrow 18 with the hands, while tube 14 is being gripped by the gripper member 20 of this invention, and optionally rotated in the direction of arrow 19.

Preferably, gripper member 20 is placed with its facing edge being just adjacent to the thinner end 22 of relatively thickened portion 24 of the tubular port 14, in the event that type of tubing is used. Port 14 may include an inner tube 25, which fits telescopically into port 14, and terminates at inner end 22 to help define the relatively thickened portion 24. Hub 27 of spike 12 defines an annular, stepped surface to press against the outer end of inner tube 25 to restrict penetration of the spike. FIG. 1 shows the gripper member 20 being placed farther down port 14 to show more clearly the thickened portion 24 and the inner end 22 with the thinner portion of port tubing 14, but in actual use the gripper member should preferably be moved outwardly to be almost flush with inner end 22. In the case of tubing which does not use the thickened portion 24, the gripper member should preferably be placed close to the pointed end of spike 12.

It can be seen how the removal by rotation of spike 12 is facilitated by the presence of gripper member 20, which rotationally retains port tubing 14.

Turning to FIGS. 2 through 4, gripper member 20 which is shown to be molded of a single, molded integral plastic piece such as a polyolefin or a styrene copolymer plastic, comprises a pair of openable and closable handles 26, 28 which are interconnnected by a thin plastic hinge member 30. Each handle defines, adjacent the hinge member 30, an arcuate recess which is preferably semi-circular as shown. Each recess 32 defines gripping projections 34 therein which serve to press into the wall of tubing 14 to prevent rotation of the tube in the closed recess 32 as in FIG. 1 when the handles are in closed position. Gripper member 20 is preferably molded in the open position shown in FIG. 2, where the handles 26, 28 are at an acute angle on the order of 45°, so that it tends to spontaneously assume the open position, for user convenience.

Additionally, a wall member 36 is provided as shown positioned longitudinally on each handle 26, 28 across each arcuate recess 32, and at the same side thereof as shown in FIG. 4. As a result of this, a flexible plastic tube may be surrounded and gripped in the arcuate recesses 32 of the handles for rotational retention as the connector member 12 is inserted into or withdrawn from tube 14. At the same time, the wall members 36 pinch the tube into closed, sealed relation when the tube occupies the recesses with the handles in closed position.

Since hinge 30 is relatively fragile, handles 26, 28 are stabilized, as they close against relative lateral motion of the respective handles out of the general plane normally occupied by both of the handles, by the following means. Handle 26 defines a generally rigid sliding surface member 38 which is positioned adjacent to and facing hinge member 30. The other handle 28 defines a generally rigid projection 40 which is adapted to abut and slide on the surface 38 as the handles are closed. Members 38 and 40 define a substantial width in the direction perpendicular to the plane normally occupied by handles 26, 28, with the result that the abutment of projection 40 on surface 38 as the handles are closed serves as a stabilizing aid to prevent the handles 26, 28 from skewing out of the plane that they normally occupy as the handles are forcefully closed on a flexible tube 14. Thus, the handles are stabilized against relative lateral motion.

Gripper member 20 also defines a locking means to hold handles 26, 28 in the closed position, to facilitate the gripping of tube 14.

Handle 28 carries at its end opposed to hinge member 30 an integral pair of pinch arms 42, 44, one of the arms 44 defining a hook member 46 having a slanted surface 48. Pinch arms 42, 44 are connected together by a flexible plastic member 50 so that arms 42, 44 may be flexed and moved relative to each other by the fingers.

The other handle 26 carries at its end opposed to hinge member 30 a detent member 52 which also defines a slanted surface 54.

Accordingly, upon closing of gripper member 20, hook member 46 and detent member 52 are capable of snapping into engagement with each other, to hold gripper member 20 in its closed position for gripping tube 14, and rotationally retaining it.

When it is desired to open the gripper member again, pinch arms 42, 44 may be squeezed, causing hook member 46 to be withdrawn from detent member 52, to permit the opening.

Gripper member 20 also defines a flange 56 defined on each of handles 26, 28, and positioned longitudinally with respect to each handle, and at one side of the handle as shown in FIG. 1, adjacent arcuate recesses 32. The effect of this is to help prevent touch contamination of the plastic tube by the fingers while the tube occupies the recesses of the handles. It can be seen that the flanges 56, when facing tube 14, serve as a barrier to prevent the fingers of the user from accidentally touching tubing 14 during manipulation.

This freedom from touch contamination is particularly important in the field of peritoneal dialysis, where extreme care must be taken for the avoidance of contamination, since peritonitis is a constant risk with this type of procedure.

As can be seen from FIG. 3, it is preferred for a space 58 to be defined between the edges of walls 36 when handles 26, 28 are in the closed position, to provide room for the collapsed tubing to fit. The width of spaces 58 is accordingly sized to permit a tight seal of the tubing without significant mechanical disruption or destruction of the structure of the tubing due to excessive pressure.

The above has been offered for illustrative purposes only, and is not intended to limit the invention of this application, which is as defined in the claims below.

That which is claimed is:

1. A gripper member which comprises: an openable and closable pair of handles interconnected by a hinge member, each handle defining, an arcuate recess positioned to face the corresponding recess of the other handle and defining gripping projections therein, and a wall member positioned longitudinally on each handle across each arcuate recess and at the same side thereof, whereby a flexible plastic tube may be surrounded and gripped in the arcuate recesses of said handles for rotational retention thereof as a connector member is inserted into or withdrawn from said tube, said wall members pinching said tube into closed, sealed relation when occupying said recesses with the handles in closed position.

2. The gripper member of claim 1 which is made of an integral, plastic piece, and said hinge member comprises a thin integral flexible plastic strip, in which one handle defines a generally rigid, sliding surface adjacent to and facing said hinge member, and the other handle defines a generally rigid projection adapted to abut and slide on said surface as the handles are closed, to stabilize said handles against relative lateral motion.

3. The gripper member of claim 1 in which one handle carries at its end opposed to said hinge member an integral pair of pinch arms and a hook member carried on one of said arms, and the other handle carries at its end opposed to said hinge member a detent member, said hook member being adapted to engage the detent member to hold said handles in closed position, said pinch arms being adapted to disengage said detent and hook members by manual pinching, to permit opening of said handles.

4. The gripper member of claim 1 in which each handle carries a flange positioned longitudinally and at one side of said handle and adjacent said arcuate recess, to prevent touch contamination by the fingers of said plastic tube while it occupies the recesses of said handles.

5. The gripper member of claim 1 in which said handles, in the unstressed, as-molded condition, assume an acute angle with respect to each other.

6. A gripper member which comprises: an openable and closable pair of handles interconnected by a hinge member, each handle defining, adjacent said hinge member, an arcuate recess positioned to face the corresponding recess of the other handle and defining gripping projections therein, and a wall member positioned longitudinally on each handle across each arcuate recess and at the same side thereof, whereby a plastic tube may be surrounded and gripped in the arcuate recesses of said handles for rotational retention thereof as a connector member is inserted into or withdrawn from said tube, said wall members pinching said tube into closed, sealed relation when in said recesses with the handles in closed position, each handle carrying a flange positioned longitudinally and at one side of said handle and adjacent said arcuate recess, to prevent touch contamination by the fingers of said plastic tube while it occupies the recesses of said handles, one handle defining a rigid, sliding surface adjacent to and facing said hinge member, and the other handle defining a rigid projection adapted to abut said slide on said surface as the handles are closed, to stabilize said handles against relative lateral motion.

7. The gripper member of claim 6 in which one handle carries at its end opposed to said hinge member an integral pair of pinch arms and a hook member carried on one of said arms, and the other handle carried at its end opposed to said hinge member a detent member, said hook member being adapted to engage the detent member to hold said handles in closed position, said pinch arms being adapted to disengage said detent and hook members by manual pinching, to permit opening of said handles.

8. The gripper member of claim 7 in which said handles, in the unstressed, as-molded condition, assume an acute angle to each other.

9. A gripper member made of an integral plastic piece, which comprises:

an openable and closeable pair of handles interconnected by a hinge member, said hinge member comprising an integral, flexible plastic strip, each handle defining, adjacent said hinge member, an arcuate recess positioned to face the corresponding recess of the other handle and defining gripper projections therein, whereby a flexible plastic tube may be surrounded and gripped in the arcuate recesses of said handles for rotational retention thereof as a connector member is inserted into or withdrawn from said tube, and in which one handle defines a generally rigid, sliding surface adjacent to and facing said hinge member, and the other handle defines a generally rigid projection adapted to abut and slide on said surface as the handles are closed, to stabilize said handles against relative lateral motion.

10. The gripper member of claim 9, which includes releasable means for retaining said handles in enclosed position for surrounding and gripping the flexible plastic tube in the arcute recesses.

11. The gripper member of claim 9, in which each handle carries a flange positioned longitudinally at one side of said handle and adjacent said arcuate recess, to prevent touch contamination by the fingers of said plastic tube while it occupies the recesses of said handles.

*12. A gripper member which comprises: an openable and closable pair of handles interconnected by a hinge member, each handle defining, an arcuate recess positioned to face the corresponding recess of the other handle, and a wall member positioned longitudinally on each handle across each arcuate recess and at the same side thereof, whereby a flexible plastic tube may be surrounded and gripped in the arcuate recesses of said handles for rotational retention thereof as a connector member is inserted into or withdrawn from said tube, said wall members pinching said tube into closed, sealed relation when occupying said recesses with the handles in closed position.*

*13. A gripper member which comprises: an openable and closable pair of handles interconnected by a hinge member, each handle defining, adjacent said hinge member, an arcuate recess positioned to face the corresponding recess of the other handle, and a wall member positioned longitudinally on each handle across each arcuate recess and at the same side thereof, whereby a plastic tube may be surrounded and gripped in the arcuate recesses of said handles for rotational retention thereof as a connector member is inserted into or withdrawn from said tube, said wall members pinching said tube into closed, sealed relation when in said recesses with the handles in closed position, each handle carrying a flange positioned longitudinally at one side of said handle and adjacent said arcuate recess, to prevent touch contamination by the fingers of said plastic tube while it occupies the recesses of said handles, one handle defining a rigid sliding surface adjacent to and facing said hinge member, and the other handle defining a rigid projection adapted to abut said slide on said surface as the handles are closed, to stabilize said handles against relative lateral motion.*

*14. The gripper member of claim 13 in which each flange is positioned on the handle at the side thereof which is opposed to the wall member of said handle.*

*15. The gripper member of claim 14 in which one handle carries at its end opposed to said hinge member an integral pair of pinch arms and a hook member carried on one of said arms, and the other handle carries at its end opposed to said hinge member a detent member, said hook member being adapted to engage the detent member to hold said handles in closed position, said pinch arms being adapted*

*to disengage said detent and hook members by manual pinching, to permit opening of said handles.*

*16. The gripper member of claim 15 in which said handles, in the unstressed, as-molded condition, assume an acute angle to each other.*

*17. The gripper member of claim 16 in which said hinge member comprises a thin integral, flexible plastic strip.*

* * * * *